United States Patent [19]
Mulla

[11] Patent Number: 5,649,565
[45] Date of Patent: Jul. 22, 1997

[54] GAS DELIVERY CIRCUIT HOLDER

[76] Inventor: Adil D. Mulla, 19 Pheasant Ridge Rd., Redding, Conn. 06896

[21] Appl. No.: 373,038

[22] Filed: Jan. 17, 1995

[51] Int. Cl.⁶ .................. F16L 3/00; A47B 96/06
[52] U.S. Cl. .................. 137/343; 24/486; 248/218.4; 248/231.71
[58] Field of Search ............. 251/143; 137/393; 24/486; 248/218.4, 231.7; 604/322, 323

[56] References Cited

U.S. PATENT DOCUMENTS

| | | | |
|---|---|---|---|
| 4,139,017 | 2/1979 | Hamilton, Sr. et al. | 137/343 |
| 4,666,111 | 5/1987 | Schuler | 248/231.71 X |
| 5,160,106 | 11/1992 | Monick | 248/231.71 |
| 5,161,764 | 11/1992 | Roney | 248/231.71 |
| 5,174,533 | 12/1992 | Pryor et al. | 248/231.71 X |
| 5,193,574 | 3/1993 | Lopez | 137/343 |
| 5,322,253 | 6/1994 | Stevens | 248/231.71 X |
| 5,326,059 | 7/1994 | Pryor et al. | 248/231.71 |
| 5,355,539 | 10/1994 | Boettger | 248/231.71 X |

*Primary Examiner*—Hoang Nguyen

[57] ABSTRACT

The invention is a holder for holding a distal gas outlet of a gas delivery circuit wherein the holder comprises: a base having an upper surface and a pose for sealably engaging the distal gas outlet of the gas delivery circuit, the post being attached to the upper surface of the base and adapted to fit the distal end of the gas delivery circuit so as to hold and seal the distal gas outlet of the gas delivery circuit.

13 Claims, 3 Drawing Sheets

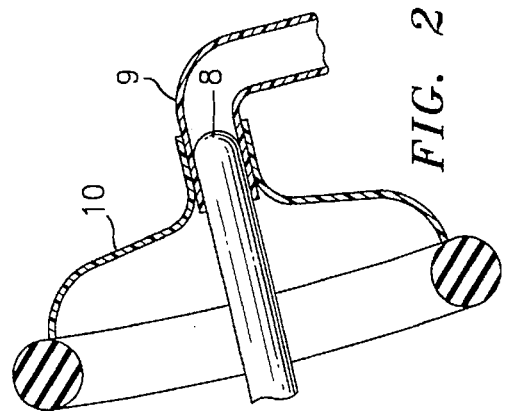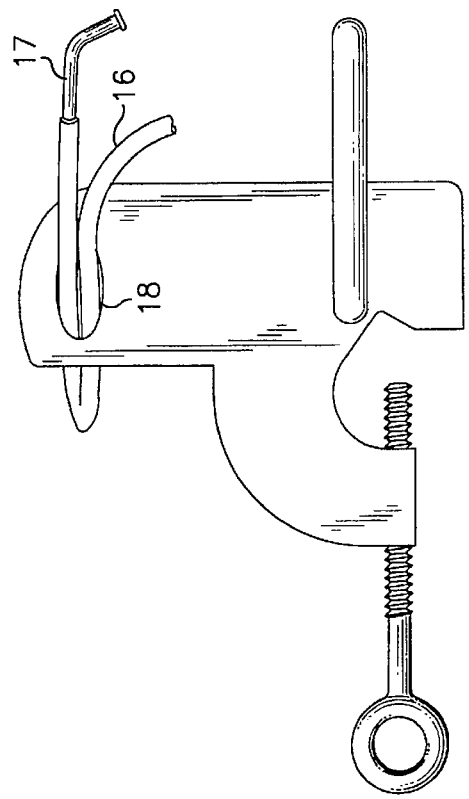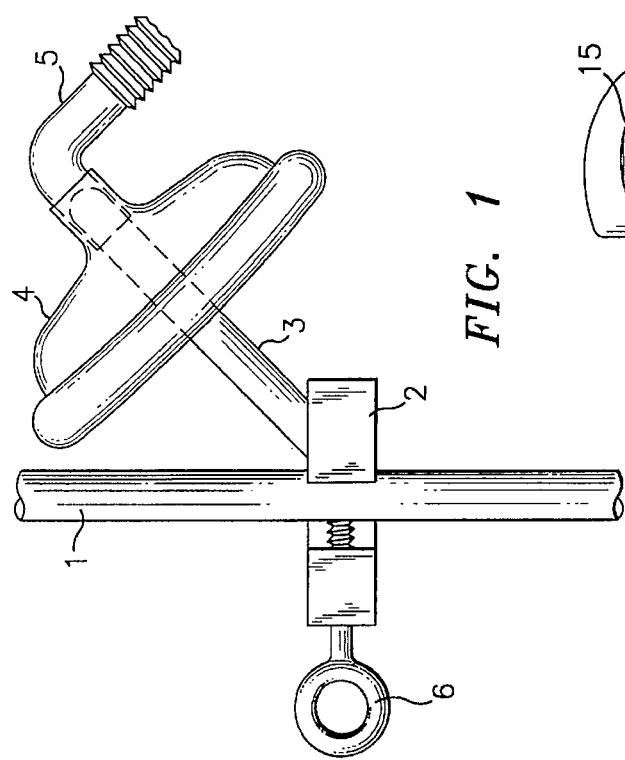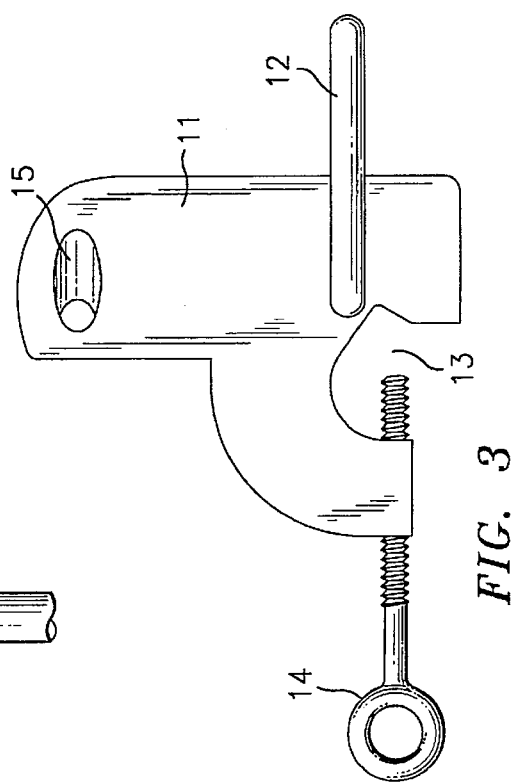
FIG. 1
FIG. 2
FIG. 3
FIG. 4

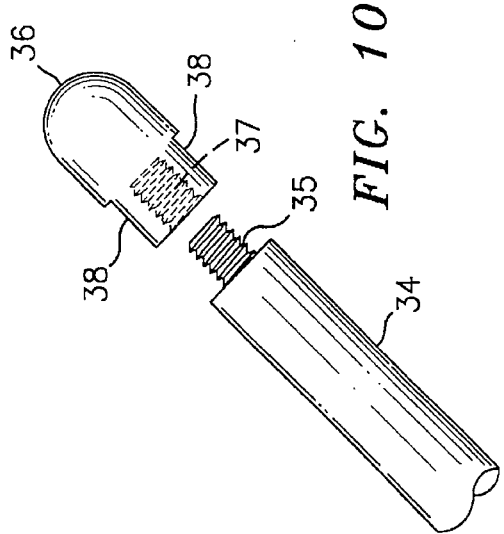
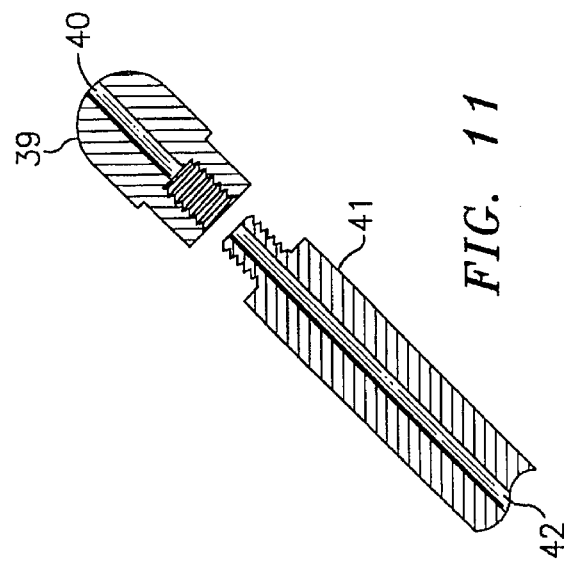
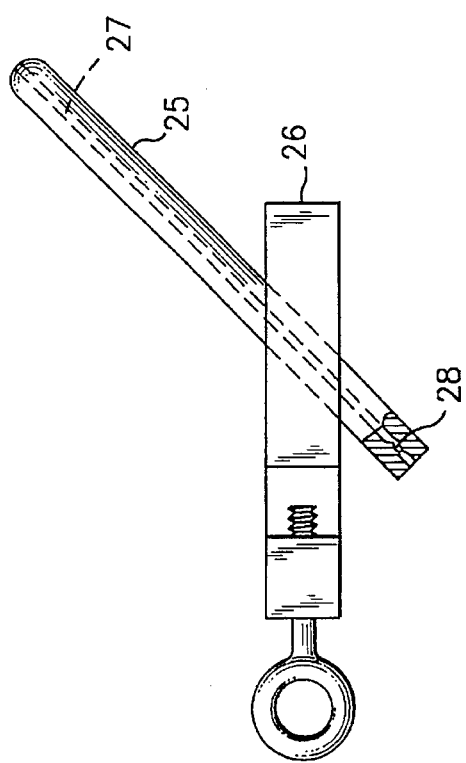
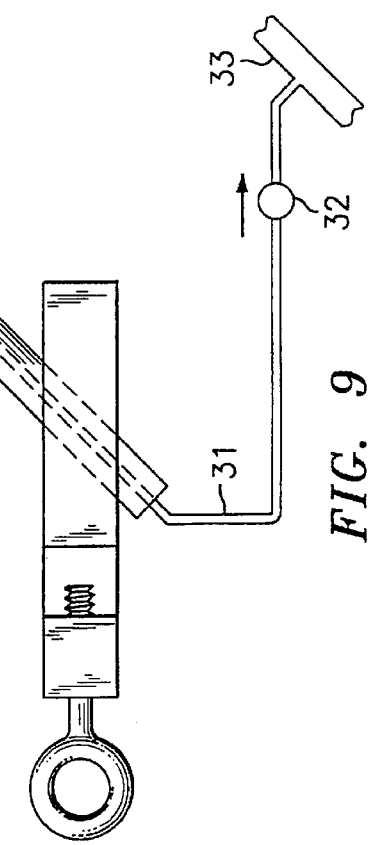

GAS DELIVERY CIRCUIT HOLDER

BACKGROUND OF THE INVENTION

The anesthetic circuit is a system of flexible hoses that is connected at one end to an anesthesia machine and to the other end via an elbow to a mask (or endotracheal tube). The anesthesia machine when activated flows anesthetic gases through the flexible hoses to the patient.

During the administration of anesthesia, many maneuvers performed by the anesthetist require temporary removal of the mask from the patients face, e.g. 1) placement of a tube into the patients esophagus or trachea, 2) positioning of head straps 3) examination and/or suction of the mouth, pharynx or larynx by the surgeon or anesthetist, etc. During such maneuvers it is not uncommon (for lack of a convenient holder) to find the circuit placed on the patients body, squeezed between the body of the anesthetist and the operating room table, or simply laying on the floor, often with components disconnected during the fall or at the time of retrieval of said circuit. There is a need for a holding device for the circuit and mask. Also, during periods of such maneuvers (and prior to placement of the mask on the patients face), anesthetic gases may be freely released into the operating room environment posing a potential health hazard to operating room personell.

Often, after the patient is anesthetized it becomes necessary to place a (endotracheal) tube into the patients windpipe, disconnect the mask from the circuit, and administer anesthetic gases directly through said tube. The mask however (now disconnected from the circuit) is required at the end of the operation when said tube is removed, or urgently if the tube is accidently dislodged. Ability to urgently locate the mask is crucial, and often a problem during complex anesthetic cases.

Availability of suction (to suck out secretions or fluids from the mouth or stomach) via a flexible tubing with a rigid or soft extention is a necessity during the administration of anesthesia. Placement of the suction tubing in a secure and use-ready manner is often a problem. Much like the anesthesia circuit, the suction tubing is often dropped to the floor for want of a convenient location for placement.

SUMMARY AND OBJECTS OF THE INVENTION

The invention is a device that enables the user of an anesthesia or other gas delivery system to temporarily and conveniently place the delivery circuit in a way that 1) it can be held securely 2) it occludes the end of the circuit to prevent the release of gases into the immediate surroundings 3) it provides for easy location of the mask and circuit 4) provides a convenient holder for the mask while the circuit is in use without the mask. 5) it provides a convenient holder for flexible suction tubing.

BRIEF DESCRIPTION OF THE DRAWINGS

The above mentioned objects of the invention will become apparent when the following drawings and accompanying descriptions are considered together.

FIG. 1 Preferred embodiment of invention in use. A perspective view with anesthetic circuit engaged.

FIG. 2 Lateral cross section of the fit between anesthesia mask over end of anesthesia circuit and fit of anesthesia circuit over the post of my invention.

FIG. 3 Top plan view of the invention with optional holder for suction tube.

FIG. 4 Top plan view with optional holder for suction tube in use.

FIG. 8 Schematic side view of a canulated version of the device with a fitted whistling alarm.

FIG. 9 Schematic side view of a canulated version of the device connected to a scavenger.

FIG. 10 Close up view of a modified post with disposable tip.

FIG. 11 Close up view of a modified post with disposable tip further modified with cannulation of the post and tip.

DETAILED DESCRIPTION OF THE PREFERED EMBODIMENT

Figure 7:
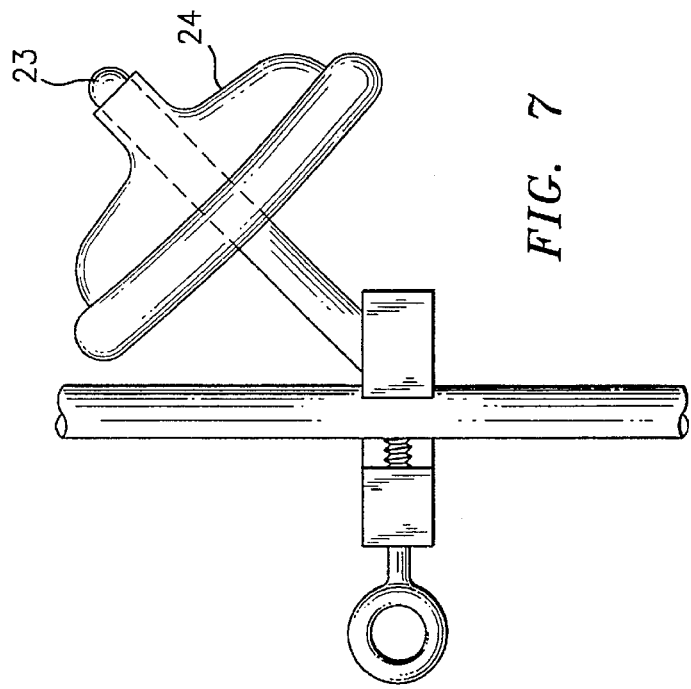
FIG. 7 Devise in use for placement of mask over post while anesthetic circuit is in use without a mask.

Refering to FIG. 1 of the drawings: this is an illustration of my invention in its preferred embodiment with an anesthetic circuit (5), with mask (4), mounted on the post (3). The invention is clamped by a suitable clamping devise (6) to an IV pole (1). Also apparent is the base (2) onto which is mounted said post at an angle of approximately 45 degrees. The optional holder for suction tubing is not visible in this illustration.

Refering to FIG. 2: the post (8) is cylindrical, of cross-sectional diameter almost equal to that of the internal diameter of the lumen of the end of the elbow (9) of the anesthetic circuit, thus permitting a snug fit of the elbow over the post. Due to such a snug fit, the egress of gases from the circuit into the ambient atmosphere is prevented. This is an important pollution control feature of the invention. The mask (10) fits OVER the external diameter of the elbow.

Refering to FIG. 3: this diagram shows a top view of the invention showing the base (11) with protruding post (12). A notched semicircular cut-out (13) and thumbscrew (14) allow for rigid attachment to an IV pole. This is accomplished by placing the pole within the cut-out and tightening the thumbscrew firmly. The purpose of such a clamping device is to allow fixation of the base onto a suitable stationary object (in this case a verticle IV pole). Such fixation permits the anesthetist to place the circuit firmly onto the post in order to get a good fit between the post and the end of the circuit. The base can alternately be affixed to any stationary object, eg: a convenient horizontal or verticle support that is part of an anesthesia machine or operating table. Alternately, any stationary object, (eg: A part of an anesthesia machine or operating room table) could act as a base, and the post can be mounted on such a base. A throughbore (15) of approximately ¾ inch at an angle of 45 degrees to the horizontal, acts as the optional suction tubing holder.

Refering to FIG. 4: This diagram shows a top view of the invention with a suction tubing (16) with suction tip (17), folded and tucked into the suction tubing holder (18). By folding the suction tubing, its lumen is occluded. Occluding the lumen is the preferred method of keeping the suction tubing available for ready use. Occlusion eliminates the constant sucking sound (which is a distraction), and maintains strong negative pressure in the tubing proximal to the point of occlusion. Though the description of this suction tubing holder in this embodiment is that of a throughbore, such a suction tubing holder could be a cut-out of quadrangular cross section into which a folded suction tubing could be tucked and secured.

A short hollow tube of circular or quadrangular cross section mounted on a base can serve the same function.

Figure 5:
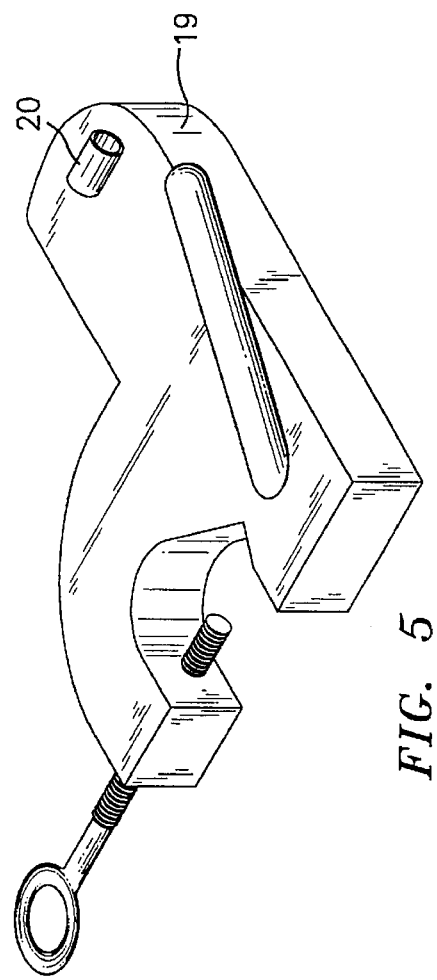
FIG. 5 Frontal view of alternate suction holder: a hollow tube of circular cross section, mounted on a base.

FIG. 5 shows an alternate design of suction tubing holder (20) comprising a short piece of rigid, hollow, open-ended tube of circular cross section mounted on the base (19).

Figure 6:
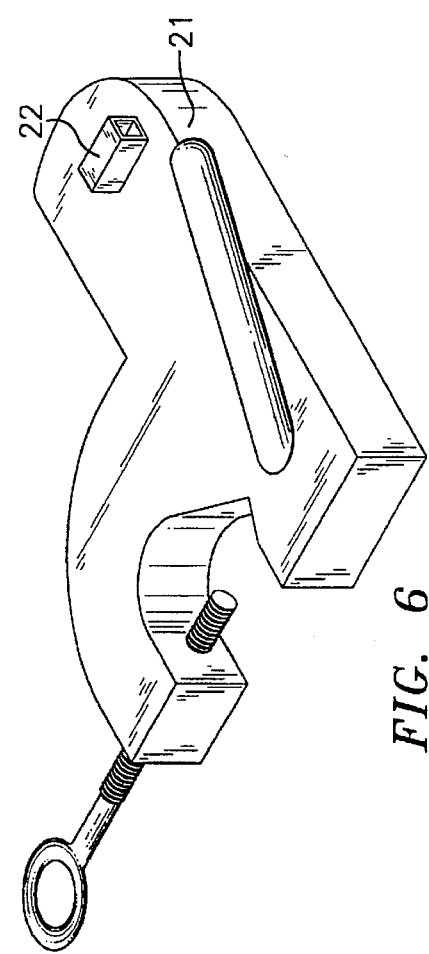
FIG. 6 Frontal view of alternate suction holder: a hollow tube of quadrangular cross section, mounted on a base.

FIG. 6 shows an alternate design of suction tubing holder (22) comprising a short piece of rigid, hollow, open-ended tube of quadrangular cross section mounted on the base (21).

Refering to FIG. 7: illustrated here is a side view of the invention with an anesthesia mask (24) placed over the post (23) for convenient holding while the circuit is in use WITHOUT the mask.

Most modern anesthesia delivery machines are equiped with a pressure relief valve that will "pop off" if the pressure in the circuit were to exceed a pre-set level. The released gases are diverted to a scavenger system for safe removal. Anesthesia machines are also equiped with a high pressure audible alarm, connected to the circuit, that is activated at a preset pressure. During engagement of the end of such a circuit to my invention, if the pressure relief valve is not left open, pressure would build up in the circuit, activating the alarm, alerting the operator to open the pressure relief valve.

FIG. 8 illustrates an alternate design of the post (25) mounted on a portion of a base (26). The post has been cannulated (27) through its center. The purpose of said cannulation is to permit the exit of gases. A "whistle" (28) that would sound when gases travel through it at a preset flow (similar to what one may find in a whistling kettle), alerts the operator to open the pressure relief valve in the anesthesia machine.

FIG. 9 is a schematic diagram that shows a variation of the post (29) which is cannulated (30), and the cannulation is connected via a tubing (31) to a scavenging system (33) for safe removal of gases. A one way valve (32), prevents the backflow of gases through the post, and into the environment.

At the end of each anesthetic use, usually, the anesthesia circuit is replaced by a new one in order to prevent cross infection between patients. It is desirable at such a time to clean the post at its point of contact with the circuit for the same reason. An alternate to cleaning the post would be to dispose of the distal portion of the post and replace it. Such a disposable part may be designed to screw on or snap onto a modified post.

FIG. 10 illustrates the distal portion of a modified post (34) with a threaded (male) end (35). A disposable tip (36) which is of appropriate external dimension to fit snuggly into the end of an anesthetic circuit, has a threaded (female) recess (37) in its base to allow it to be screwed onto the post. Two flat cut-outs on either side of the outer circumference of the disposable tip will allow the application of an open wrench to facilitate its removal in the event that it was accidentally overtightened at the time of fixation on the post.

An adaptation of the disposable tip and matching modified post for the venting of gases (as evident in the descriptions of FIGS. 8 and 9) is shown in FIG. 11. The schematic diagram in FIG. 11 shows a modified post (41), cannulated (42) so that when the modified tip (39) is screwed onto the post, the cannulation (40) in the tip will align with that in the post to form a single passage for the exit of gases.

While I have illustrated and described my invention by specific embodiments, it is to be understood that numerous changes and modifications maybe made therein without departing from the spirit and scope of the invention as defined in the following claims.

I claim:

1. A holder for holding a distal gas outlet of a gas delivery circuit wherein the holder comprises: a base having an upper surface and a post means for sealably engaging the distal gas outlet of the gas delivery circuit, the post means being attached to the upper surface of the base and adapted to fit the distal gas outlet of the gas delivery circuit so as to hold and seal the distal gas outlet of the gas delivery circuit.

2. A holder according to claim 1, wherein a part of the post means is removeable for disposal and replacement.

3. A holder according to claim 1, wherein the post means is cannulated to provide a gas passage, and further comprising means for escape of gas through the passage when under a pressure predetemined to be excessive.

4. A holder according to claim 3, further comprising an alarm device connected to the passage for indicating release of pressure.

5. A holder according to claim 3, further comprising a gas scavenging device for safe removal of gasses from the passage.

6. A holder according to claim 1, wherein the base has a throughbore for holding a folded suction catheter.

7. A holder according to claim 1, wherein the base has a hollow cylindrical appendage for holding a folded suction catheter.

8. A holder according to claim 1, wherein the base has a quadrangular cut-out for holding a folded suction catheter.

9. A holder according to claim 1, wherein the base has a quadrangular hollow appendage for holding a folded suction catheter.

10. A holder according to claim 1, further comprising means for securing the base to a vertical support.

11. A holder according to claim 1, further comprising means for securing the base to a horizontal support.

12. A holder according to claim 1, wherein the post means comprises a post member extending from the base and having a substantially smooth contoured end portion for sealably and releasably engaging the distal gas outlet of the gas delivery circuit.

13. A holder according to claim 1, wherein the post means includes a body portion and an end portion for sealably engaging the distal gas outlet, and further comprising threaded means for releasably attaching the end portion to the body portion whereby the end portion is removable for disposal and replacement.

* * * * *